US00PP18421P2

(12) United States Plant Patent
Sakazaki

(10) Patent No.: US PP18,421 P2
(45) Date of Patent: Jan. 15, 2008

(54) ***CALIBRACHOA* PLANT NAMED 'USCALI212-1'**

(50) Latin Name: ***Calibrachoa* sp.**
Varietal Denomination: USCALI212-1

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 11/520,924

(22) Filed: Sep. 14, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette Para
(74) *Attorney, Agent, or Firm*—C. A. Whealy

(57) ABSTRACT

A new and distinct cultivar of *Calibrachoa* plant named 'USCALI212-1', characterized by its semi-upright to outwardly spreading growth habit; mounded plant habit; freely branching and flowering habit; relatively large soft pink-colored flowers with red purple-colored centers; good garden performance; and resistance to *Thielaviopsis*.

1 Drawing Sheet

Botanical designation: *Calibrachoa* sp.
Cultivar denomination: 'USCALI212-1'.

BACKGROUND OF THE INVENTION

The present invention relates to a new and distinct cultivar of *Calibrachoa,* botanically known as *Calibrachoa* sp. and hereinafter referred to by the name 'USCALI212-1'.

The new *Calibrachoa* is a product of a planned breeding program conducted by the Inventor in Hikone, Shiga, Japan. The objective of the breeding program is to create new heat-tolerant and disease-resistant *Calibrachoa* cultivars with densely mounding plant habit and numerous and attractive flowers.

The new *Calibrachoa* originated from a cross-pollination made by the Inventor on Apr. 16, 2003 in Hikone, Shiga, Japan of a proprietary seedling selection of *Calibrachoa* sp. identified as code number C67-1, not patented, as the female, or seed, parent with a proprietary seedling selection of *Calibrachoa* sp. identified as code number CJ03-051, not patented, as the male, or pollen, parent. The new *Calibrachoa* was discovered and selected by the Inventor as a single flowering plant within the progeny of the stated cross-pollination in a controlled environment in Gensingen, Germany on Jun. 4, 2004.

Asexual reproduction of the new *Calibrachoa* by terminal cuttings in a controlled environment in Gensingen, Germany since Jun. 5, 2004 has shown that the unique features of this new *Calibrachoa* are stable and reproduced true to type in successive generations.

SUMMARY OF THE INVENTION

The cultivar USCALI212-1 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'USCALI212-1'. These characteristics in combination distinguish 'USCALI212-1' as a new and distinct cultivar of *Calibrachoa:*

1. Semi-upright to outwardly spreading growth habit; mounded plant habit.
2. Freely branching habit.
3. Freely flowering habit.
4. Relatively large soft pink-colored flowers with red purple-colored centers.
5. Good garden performance.
6. Resistant to *Thielaviopsis.*

Plants of the new *Calibrachoa* can be compared to plants of the female parent selection. Plants of the new *Calibrachoa* differ from plants of the female parent selection in the following characteristics:

1. Plants of the new *Calibrachoa* are more outwardly spreading than and not as upright as plants of the female parent selection.
2. Plants of the new *Calibrachoa* and the female parent selection differ in flower color as plants of the female parent selection have purple-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are more upright than and not as creeping as plants of the male parent selection.
2. Plants of the new *Calibrachoa* and the male parent selection differ in flower color as plants of the male parent selection do not have red purple-colored flower centers.

Plants of the new *Calibrachoa* can be compared to plants of the cultivar Sunbelkupi, disclosed in U.S. Plant Pat. No. 10,287. In side-by-side comparisons conducted in Gensingen, Germany, plants of the new *Calibrachoa* differed from plants of the cultivar Sunbelkupi in the following characteristics:

1. Plants of the new *Calibrachoa* were more upright than and not as creeping as plants of the cultivar Sunbelkupi.
2. Plants of the new *Calibrachoa* and the Sunbelkupi differed in flower color as plants of the cultivar Sunbelkupi had red purple-colored flowers.

Plants of the new *Calibrachoa* can also be compared to plants of the cultivar Kakegawa S8, disclosed in U.S. Plant Pat. No. 12,508. In side-by-side comparisons conducted in Gensingen, Germany, plants of the new *Calibrachoa* differed from plants of the cultivar Kakegawa S8 in the following characteristics:

1. Plants of the new *Calibrachoa* were more upright than and not as creeping as plants of the cultivar Kakegawa S8.
2. Plants of the new *Calibrachoa* and the Kakegawa S8 differed in flower color as plants of the cultivar Kakegawa S8 had darker pink-colored flowers.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the bottom of the sheet comprises a side perspective view of a typical flowering plant of 'USCALI212-1' grown in a container.

The photograph at the top of the sheet comprises a close-up of typical flowers of 'USCALI212-1'.

DETAILED BOTANICAL DESCRIPTION

The photographs and following observations, measurements and values describe plants grown in Bonsall, Calif., under commercial practice during the summer in a polyethylene-covered greenhouse with day temperatures ranging from 18° C. to 32° C. and night temperatures ranging from 13° C. to 24° C. Rooted young plants were grown for about seven weeks with one plant per 15-cm container. In the following description, color references are made to The Royal Horticultural Society Colour Chart, 1995 Edition, except where general terms of ordinary dictionary significance are used.

Botanical classification: *Calibrachoa* sp. cultivar USCALI212-1.

Parentage:

*Female, or seed, parent.*—Proprietary seedling selection of *Calibrachoa* sp. identified as code number C67-1, not patented.

*Male, or pollen, parent.*—Proprietary seedling selection of *Calibrachoa* sp. identified as code number CJ03-051, not patented.

Propagation:

*Type.*—By terminal cuttings.

*Time to produce a rooted young plant, summer.*—About three weeks at temperatures of 20° C.

*Time to produce a rooted young plant, winter.*—About four weeks at temperatures of 20° C.

*Root description.*—Fine; white in color.

*Rooting habit.*—Freely branching; dense.

Plant description:

*Plant and growth habit.*—Semi-upright to outwardly spreading, mounding growth habit. Freely branching habit with about ten primary lateral branches each with multiple secondary lateral branches; pinching is typically not required. Vigorous growth habit and moderately rapid growth rate.

*Plant height.*—About 19 cm.

*Plant diameter.*—About 58 cm.

Lateral branch description:

*Length.*—About 26 cm.

*Diameter.*—About 3.5 mm.

*Internode length.*—About 1.6 cm.

*Strength.*—Strong.

*Aspect.*—Initially upright to outwardly spreading.

*Texture.*—Pubescent.

*Color.*—144A.

Foliage description:

*Arrangement.*—Before flowering, alternate, simple; after flowering, opposite, simple.

*Length.*—About 2.5 cm.

*Width.*—About 8 mm.

*Shape.*—Elliptical.

*Apex.*—Broadly acute to nearly rounded.

*Base.*—Attenuate.

*Margin.*—Entire.

*Texture, upper and lower surfaces.*—Minute pubescence; slightly coarse.

*Venation pattern.*—Pinnate; arcuate.

*Color.*—Developing foliage, upper and lower surfaces: 146A. Fully expanded foliage, upper surface: 147A; venation, 147B. Fully expanded foliage, lower surface: 146A; venation, 146B.

*Petiole.*—Length: About 2 mm. Diameter: About 2 mm. Texture, upper and lower surfaces: Minute pubescence. Color, upper and lower surfaces: 147B.

Flower description:

*Flower arrangement and habit.*—Salverform flowers arranged singly arising from leaf axils. Freely flowering habit with usually about 44 open flowers and flower buds per lateral branch. Flowers persistent. Flowers face mostly outwardly.

*Fragrance.*—None detected.

*Natural flowering season.*—Plants of the new *Calibrachoa* initiate and develop flowers about four weeks after planting. Plants flower continuously from April to October in Southern California.

*Flower longevity.*—Individual flowers last about one week on the plant.

*Flower diameter.*—About 2.5 cm.

*Flower length (height).*—About 2.3 cm.

*Flower throat diameter.*—About 5 mm by 6 mm.

*Flower tube diameter.*—About 2.5 mm.

*Flower tube length.*—About 1.6 cm.

*Flower bud.*—Shape: Elongated oblong. Length: About 2 cm. Diameter: About 4 mm. Color: 155B.

*Corolla.*—Arrangement: Five petals fused at the base and opening into a flared trumpet. Petal length from throat: About 1.1 cm. Petal lobe width: About 1.3 cm. Petal shape: Roughly obovate. Petal apex: Very slightly acuminate. Petal margin: Entire. Petal texture, upper and lower surfaces: Smooth, velvety. Throat texture: Smooth, velvety. Tube texture: Minute pubescence. Color: Petal, when opening, upper surface: 155D blushed with 69B. Petal, when opening, lower surface: 155D. Petal, fully opened, upper surface: 65B to 65C; towards the throat, 64B;

midvein, 64C; color becoming closer to 65D with development. Petal, fully opened, lower surface: 65D; midvein, 64C. Throat: 12A; venation, 64D. Tube: 10A; venation, 183D.

*Calyx.*—Arrangement: One star-shaped calyx tube with five sepals fused at the base per flower. Sepal length: About 8 mm. Sepal width: About 2.5 mm. Sepal shape: Narrowly lanceolate. Sepal apex: Acute. Sepal margin: Entire. Sepal texture, upper and lower surfaces: Minute pubescence. Color, upper and lower surfaces: 143A.

*Peduncles.*—Length: About 1.6 cm. Diameter: About 1 mm. Angle: About 45° to 60° from stem axis. Strength: Strong. Texture: Minute pubescence. Color: 144A.

*Reproductive organs.*—Stamens: Quantity/arrangement: Five per flower. Anther shape: Ovoid. Anther length: About 1 mm. Anther color: 4A. Pollen amount: Scarce. Pollen color: 4A. Pistils: Quantity: One per flower. Pistil length: About 1.3 cm. Style length: About 1.1 cm. Style color: 144D. Stigma shape: Oval. Stigma color: 144B. Ovary color: 144D. Seed/fruit: Seed and fruit development have not been observed on plants of the new *Calibrachoa.*

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have not been observed to be resistant to *Thielaviopsis.* Plants of the new *Calibrachoa* have not been observed to be resistant to pests and other pathogens common to *Calibrachoa.*

It is claimed:

1. A new and distinct *Calibrachoa* plant named 'USCALI212-1' as illustrated and described.

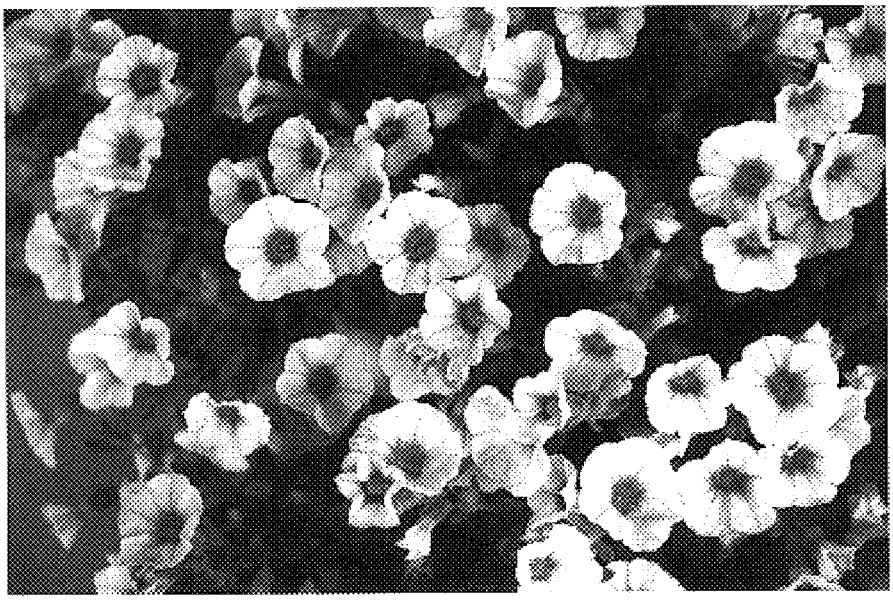
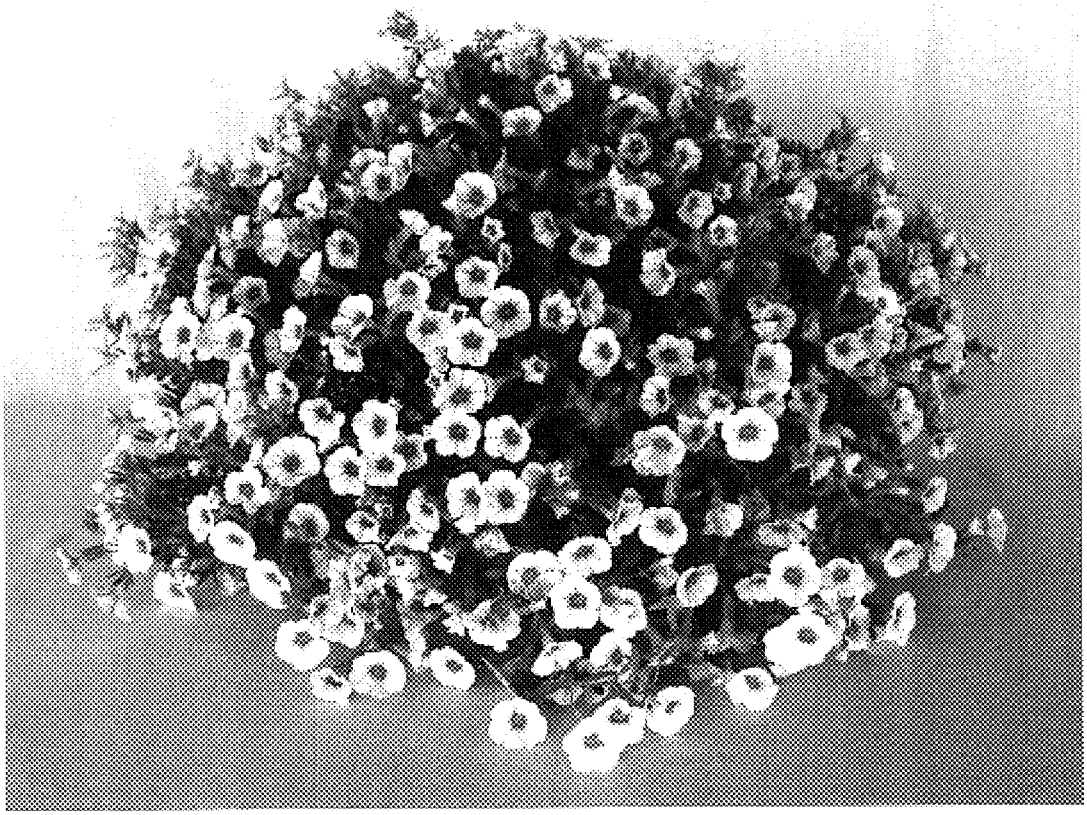

* * * * *